United States Patent
Margulies

(10) Patent No.: US 11,957,676 B1
(45) Date of Patent: *Apr. 16, 2024

(54) CONTROLLED RELEASE FORMULATION AND MINIMALLY INVASIVE METHOD OF ADMINISTRATION TO LOCALLY TREAT CANCER

(71) Applicant: Zetagen Therapeutics, Inc., Syracuse, NY (US)

(72) Inventor: Bryan S. Margulies, Liverpool, NY (US)

(73) Assignee: Zetagen Therapeutics, Inc., Syracuse, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/366,414

(22) Filed: Aug. 7, 2023

(51) Int. Cl.
*A61K 31/485* (2006.01)
*A61K 47/02* (2006.01)
*A61K 47/36* (2006.01)

(52) U.S. Cl.
CPC ............ *A61K 31/485* (2013.01); *A61K 47/02* (2013.01); *A61K 47/36* (2013.01)

(58) Field of Classification Search
CPC .................................................. A61K 31/485
See application file for complete search history.

(56) References Cited

U.S. PATENT DOCUMENTS

| | | | |
|---|---|---|---|
| 5,075,109 A | 12/1991 | Tice et al. | |
| 6,384,044 B1 | 5/2002 | Bihari | |
| 6,713,488 B2 * | 3/2004 | Sadee ................... | A61K 31/485 514/282 |
| 11,471,454 B2 | 10/2022 | Margulies et al. | |
| 2007/0197573 A1 | 8/2007 | Sadee et al. | |
| 2019/0093109 A1 * | 3/2019 | Thakur ............... | C12N 15/1138 |
| 2021/0030746 A1 * | 2/2021 | Margulies ............. | A61K 47/20 |
| 2021/0228571 A1 | 7/2021 | Margulies et al. | |
| 2022/0016312 A1 * | 1/2022 | Margulies ............ | A61L 27/042 |

FOREIGN PATENT DOCUMENTS

| | | | | |
|---|---|---|---|---|
| WO | WO-9736608 A1 * | 10/1997 | ........... | A61K 31/485 |
| WO | WO-2021/011529 | 1/2021 | | |
| WO | WO-2021011529 A1 * | 1/2021 | ........... | A61K 31/485 |
| WO | WO-2022/015364 A1 | 1/2022 | | |

OTHER PUBLICATIONS

U.S. Appl. No. 18/047,078, filed Oct. 17, 2022, Margulies; Bryan S.*
U.S. Appl. No. 18/366,439, filed Aug. 7, 2023, Margulies; Bryan S.*
Javidan et al., A novel controlled release drug delivery system for naltrexone administration combined with intermittent morphine to induce antinociception, Journal of Drug Delivery Science and Technology, vol. 24, Issue 4, 2014, pp. 413-417.*
Zagon et al., "The biology of the opioid growth factor receptor (OGFr)," Brain Research Reviews, 2002, 38:351-376.
Coussens et al., "Small-Molecule Screens: A Gateway to Cancer Therapeutic Agents with Case Studies of Food and Drug Administration-Approved Drugs," Pharmacological Reviews, Oct. 2017, 69(4):479-496.
Gyanani et al., "Challenges of Current Anticancer Treatment Approaches with Focus on Liposomal Drug Delivery Systems," Pharmaceuticals, 2021, 14(9):835, 1-27.

* cited by examiner

*Primary Examiner* — Svetlana M Ivanova
(74) *Attorney, Agent, or Firm* — Foley & Lardner LLP

(57) ABSTRACT

A controlled release formulation comprising an opioid growth factor receptor (OGFR) antagonist and at least one pharmaceutically acceptable carrier has been developed, which is useful for treating cancer when locally administered at a disease site.

16 Claims, 2 Drawing Sheets
Specification includes a Sequence Listing.

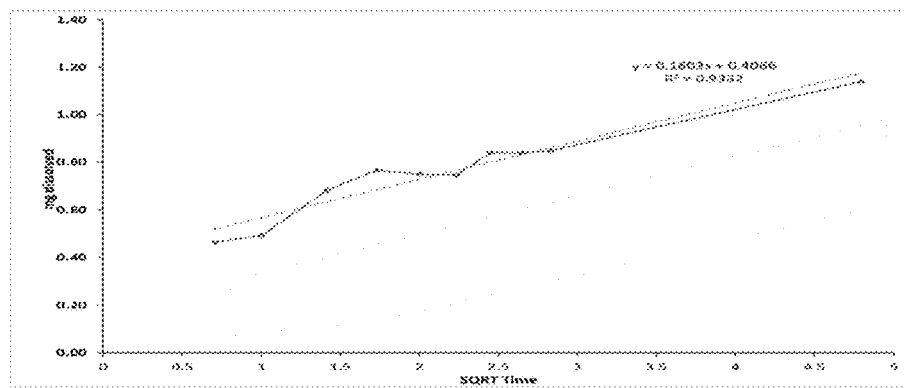

Figure 1: Small Molecule Release Rate evaluated using ultra performance liquid chromatography (UPLC). The equation for the line (dotted line), y = 0.1603x + 0.4066, had an $R^2$ = 0.9332, that the empirical data (solid line) fits to a line well. This equation was used to determine the rate of the naloxone as well as how much naloxone eluted out of the ZM001 material over 24-hours.

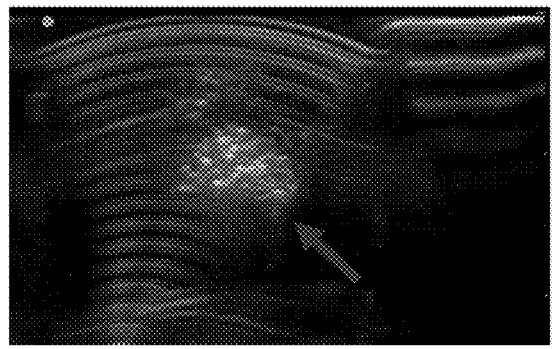

Figure 2: The controlled release formulation viewed using ultrasound (arrow).

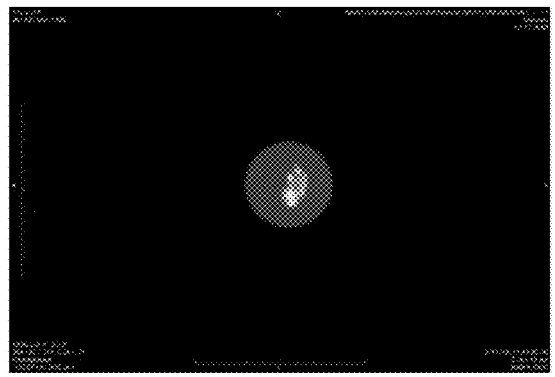

Figure 3: CT image of the controlled formulation (white material inside the gray circle).

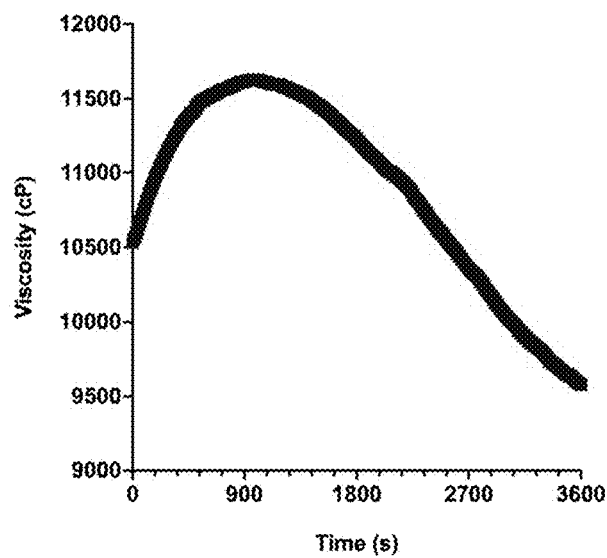
Figure 4: Viscosity as a function of time. The gelation point is the maximum viscosity, which was achieved at 1000-sec.
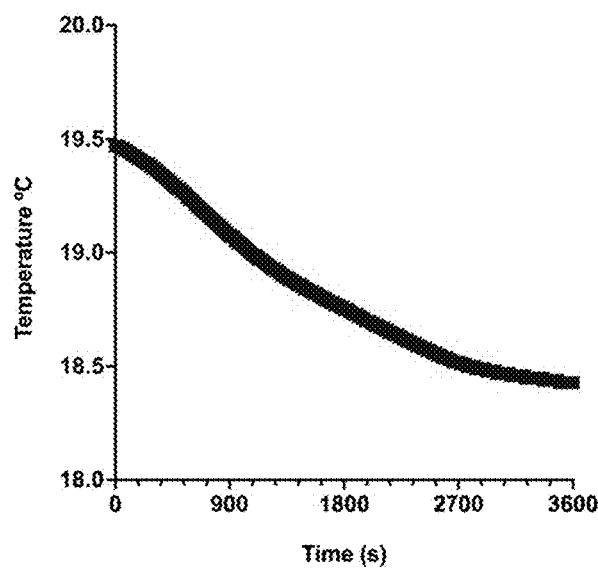
Figure 5: Temperature decreased as a function of time, e.g., the material is endothermic.

SEQUENCE LISTING

```
Sequence total quantity: 4
SEQ ID NO: 1            moltype = AA  length = 5
FEATURE                 Location/Qualifiers
source                  1..5
                        mol_type = protein
                        organism = synthetic construct
SEQUENCE: 1
YGGFM                                                                     5

SEQ ID NO: 2            moltype = AA  length = 5
FEATURE                 Location/Qualifiers
source                  1..5
                        mol_type = protein
                        organism = synthetic construct
SEQUENCE: 2
YGGFL                                                                     5

SEQ ID NO: 3            moltype = AA  length = 8
FEATURE                 Location/Qualifiers
source                  1..8
                        mol_type = protein
                        organism = synthetic construct
SITE                    1
                        note = D-amino acid
SITE                    4
                        note = D-amino acid
SITE                    7
                        note = Penicillamine
SITE                    8
```

```
                     note = Amine modified residue
SEQUENCE: 3
FCYWKTXT                                                                  8

SEQ ID NO: 4        moltype = AA  length = 50
FEATURE             Location/Qualifiers
source              1..50
                    mol_type = protein
                    organism = synthetic construct
SEQUENCE: 4
QSALDYFMFA VRCRHQRRQL VHFAWEHFRP RCKFVWGPQD KLRRFKPSSL                    50
```

CONTROLLED RELEASE FORMULATION AND MINIMALLY INVASIVE METHOD OF ADMINISTRATION TO LOCALLY TREAT CANCER

SEQUENCE LISTING

The instant application contains a Sequence Listing which has been submitted electronically in XML format and is hereby incorporated by reference in its entirety. Said XML copy, created on Jul. 24, 2023, is named 118922-0250_SL.xml and is 5,597 bytes in size.

FIELD

The present invention relates in general to pharmaceutical formulations, their uses for treating diseases and their methods of making and more specifically to controlled release pharmaceutical formulations, their uses, which may involve minimally invasive administration, as well as their methods of making.

SUMMARY

An embodiment of the present invention is a controlled release formulation comprising at least 10 mM of an opioid growth factor receptor (OGFR) antagonist and at least one pharmaceutically acceptable carrier. Preferably, the controlled release formulation is in the form of a gel, which can be injected. In a preferred embodiment, a controlled release formulation is prepared by combining a powder component and a solution component comprising a diluent and the OGFR antagonist. In a preferred embodiment, before use, the diluent is added to the powder component and mixed until gelling occurs. Preferably, the powder component is added to the solution component in a ratio of 6:1 to 8:1. After combining the components, the controlled release formulation is mixed until gelling occurs. Preferably, the controlled release formulation is hemostatic, is in a form that can be injected using a syringe intratumorally, and after administration to a patient can be viewed using ultrasound and computed tomography.

Another embodiment is a method of treating a cancer comprising locally administering at a site of a subject in need thereof an effective amount of a controlled release formulation comprising at least 10 mM of an opioid growth factor receptor (OGFR) antagonist and at least one pharmaceutically acceptable carrier.

FIGURES

FIG. 1 shows release rate evaluated using liquid chromatography of formulation ZM001.

FIG. 2 shows formulation ZM001 viewed using ultrasound (red arrow).

FIG. 3 shows a CT image of formulation ZM001 (white material inside the gray circle).

FIG. 4 shows viscosity as a function of time for formulation ZM001. The gelation point is the maximum viscosity, which was achieved at 1000-sec.

FIG. 5 shows temperature decrease as a function of time for formulation ZM001, which indicates that the formulation is endothermic.

DETAILED DESCRIPTION

As used in this disclosure and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

All numerical designations, e.g., pH, temperature, time, concentration, amounts, and molecular weight, including ranges, are approximations which are varied (+) or (−) by 10%, 1%, or 0.1%, as appropriate. It is to be understood, although not always explicitly stated, that all numerical designations may be preceded by the term "about." It is also to be understood, although not always explicitly stated, that the reagents described herein are merely exemplary and that equivalents of such are known in the art.

The term "comprising" or "comprises" is intended to mean that the compositions and methods include the recited elements, but do not exclude others. "Consisting essentially of," when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other the ingredients and substantial method steps recited by the claims. Embodiments defined by each of these transition terms are within the scope of this invention.

As used here, the term "antagonist" is used interchangeably with "inhibitor" and refers to a substrate that blocks or suppresses the activity, function, effect, or expression of a target. In some embodiments, the target is a compound, a protein, a gene, a cell, or an agent. As used herein, the term "expression" refers to the amount a living cell produces of a target. In some embodiments, the inhibitor suppresses expression of a target gene or protein. In some embodiments, the inhibitor includes a compound that prevents binding of another molecule to an enzyme or molecular pump. In some embodiments, the inhibitor is a compound that causes down-regulation of the enzyme. In some embodiments, the inhibitor can be a competing or non-competing inhibitor.

The term "administering" as used herein includes prescribing for administration as well as actually administering, and includes physically administering by the subject being treated or by another. As used herein "subject," "patient," or "individual" refers to any subject, patient, or individual, and the terms are used interchangeably herein. In this regard, the terms "subject," "patient," and "individual" includes mammals, and, in particular humans. When used in conjunction with "in need thereof," the term "subject," "patient," or "individual" intends any subject, patient, or individual having or at risk for a specified symptom or disorder.

As used herein, the phrase "therapeutically effective" or "effective" in context of a "dose" or "amount" means a dose or amount that provides the specific pharmacological effect for which the compound or compounds are being administered. It is emphasized that a therapeutically effective amount will not always be effective in achieving the intended effect in a given subject, even though such dose is deemed to be a therapeutically effective amount by those of skill in the art. For convenience only, exemplary dosages are provided herein. Those skilled in the art can adjust such amounts in accordance with the methods disclosed herein to treat a specific subject suffering from a specified symptom or disorder. The therapeutically effective amount may vary based on the route of administration and dosage form.

The term "treating" or "treatment" covers the treatment of a cancer described herein, in a subject, such as a human, and includes (i) inhibiting a cancer, i.e., arresting its development; (ii) relieving a cancer or disorder, i.e., causing regression of the cancer; (iii) slowing progression of the cancer; and/or (iv) inhibiting, relieving, or slowing progression of one or more symptoms of the cancer. For example, treatment of a cancer includes, but is not limited to, elimination of the cancer or the condition caused by the cancer, remission of the tumor, inhibition of the cancer, or reduction or elimination of at least one symptom of the tumor.

The term "analog" refers to a compound in which one or more individual atoms or functional groups have been replaced, either with a different atom or a different functional group, generally giving rise to a compound with similar properties. In some aspect, the analog refers to a structure that is similar to another but differs in one or two components.

The term "derivative" refers to a compound that is formed from a similar beginning compound by attaching another molecule or atom to the beginning compound. Further, derivatives, according to the invention, encompass one or more compounds formed from a precursor compound through addition of one or more atoms or molecules or through combining two or more precursor compounds.

The disclosure relates to a controlled release formulation of an opioid growth factor receptor (OGFR). The controlled release formulation may also include at least one pharmaceutically acceptable carrier.

Opioid Growth Factor Receptor (OGFR) Antagonists

By "Opioid Growth Factor Receptor (OGFR) antagonist" is meant any molecule that inhibits, suppresses or causes the cessation of at least one OGFR-mediated biological activity such as naloxone or a functional derivative thereof.

In some embodiments, an OGFR antagonist may be an OGFR binding antagonist, namely, a molecule that, interferes with, blocks or otherwise prevents the interaction or binding of the met5-ligand (OGF) to the OGFR. Met-5 is derived from the pro-hormone pro-enkephalin (PENK).

An OGFR binding antagonist may compete with the met5-ligand for binding to the OGFR on the surface of the nuclear membrane, thereby interfering with, blocking or otherwise preventing the binding of the met5-ligand to the OGFR, without triggering the downstream signaling that would otherwise be induced by the binding of the met5-ligand to the OGFR. Alternatively, an OGFR binding antagonist may bind to or sequester pro-enkephalin (PENK) or the met5-ligand with sufficient affinity and specificity to substantially interfere with, block or otherwise prevent binding of met5-ligand to the OGFR, thereby inhibiting, suppressing or causing the cessation of at least one OGFR-mediated biological activity. Generally speaking, OGFR binding antagonists may be large molecules (e.g., antibodies) or small molecules (e.g., compounds of a molecular weight of less than 15-kD, 12-kD, 10-kD or even 8-kD), and may be a polypeptide, nucleic acid, or a synthetic small molecule compound. OGFR binding antagonists may be identified with any in vitro assay readily selected by one of skill in the art. For example, OGFR antagonists may be identified using the methods described in Zagon et al., Brain Research Reviews, 2002, 38(3):351-76. Other suitable OGFR antagonists are disclosed in PCT patent application publications Nos. WO2021/011529; WO2022/015364; U.S. patent application publications Nos. 2019-0093109; 2021-0030746; 2021-0228571; 2022-0016312; and U.S. Pat. No. 11,471,454.

In one embodiment, the OGFR binding antagonist may be naloxone or a functional derivative thereof, naltrexone or a functional derivative thereof, or a combination thereof.

As used herein, a "functional derivative" refers to a derivative or analog that is structurally and functionally analogous to the originating molecule (e.g., maintains the function of naltrexone or naloxone as an OGFR antagonist). Naloxone and naltrexone analogs can be synthesized using standard synthetic procedures such as those described in March J., Advanced Organic Chemistry, 3rd Ed. (1985). Examples of naltrexone and naloxone functional derivatives include salt forms, e.g., naloxone hydrochloride dihydrate or naltrexone hydrochloride. Additional examples of naltrexone and naloxone functional derivatives suitable for use in the present methods include naltrexone and naloxone analogs disclosed in U.S. Patent Application Publication No. 2007/0197573 A1, U.S. Pat. No. 6,713,488, for example.

In another embodiment, an OGFR binding antagonist may be derived from oxymorphone and binds to the OGFR, which includes naloxone, naltrexone, nalorphine, naloxonazine, levallorphan, nalmefene, cyprodime, cyclorphan, cyclazocine, oxilorphan, LY113878, MR2266, diprenorphine, WIN 44,441-3, naltindole, or norbinaltorphimine.

In still another embodiment, an OGFR binding antagonist may be derived from trans-3,4-dimethyl-4-phenylpiperidine and binds to the OGFR, which includes LY99335, LY25506, LY117413, or LY255582. In another embodiment, an OGFR binding antagonist is derived from the met5-enkephalin or leu-enkephalin peptides, binds to the OGFR, and minimally includes the following amino acid sequences as a means of targeting the OGFR: Tyr-Gly-Gly-Phe-Met (SEQ ID NO: 1) for those derived from met5-enkephalin or Tyr-Gly-Gly-Phe-Leu (SEQ ID NO: 2) for those derived from the leu-enkephalin.

In still another embodiment, an OGFR binding antagonist is derived from the peptide antagonist 101174864 (N,N-diallyl-Tyr-Aib-Aib-Phe-Leu-OH; Aib=aminoisobutyticacid) or somatostatin analog CTP(D-Phe-Cys-Tyr-D-Trp-Lys-Thr-Pen-Thr-NH.sub.2, SEQ ID NO: 3).

In other embodiments, the OGFR antagonist, instead of being an OGFR binding antagonist, is a molecule that disrupts the nuclear localization sequence found within OGFR: 251 QSALDYFMFAVR-CRHQRRQLVHFAWEHFR-PRCKFVWGPQDKLRRFKPSSL (SEQ ID NO: 4).

In still other embodiments, the OGFR antagonist employed in the present methods is a small-hairpin RNA (shRNA) or a small-interfering RNA (siRNA) directed against the OGFR gene and effective in disrupting OGFR gene expression.

The OGFR antagonists described herein may be administered individually or in combination. Suitable combinations include, for example, naloxone and naltrexone; naloxone and/or naltrexone, in combination with another OGFR binding antagonist or another OGFR antagonist.

Cancer

In some embodiments, the controlled release formulation may be used for treating a cancer.

Cancer may refer to a condition in which abnormal cells divide without control and can invade nearby tissues.

In some embodiments, the cancer may be osteosarcoma, breast cancer, lung cancer, prostate cancer, or brain cancer. In some embodiments, the cancer may be a carcinoma, i.e., a cancer that arises from tissue that functions to line, cover, or act as a barrier for internal organs, such as the skin or breast epithelium. In some embodiments, the cancer may be sarcoma, i.e., a connective tissue cancer that can begin in bone, cartilage, fat, muscle, or other connective or supportive tissue. In some embodiments, the cancer may be a hematological cancer, i.e., a blood cancer that starts in or includes blood-forming tissue, such as the bone marrow, and causes large numbers of abnormal blood cells to be produced and enter the blood. In some embodiments, the cancer is a lymphoma or multiple myeloma, i.e., a cancer that begin in the cells of the immune system. In some embodiments, the cancer may be a central nervous system cancer, i.e., a cancer that begin in a tissue of the brain and/or spinal cord. In some embodiments, the cancer is one or more of pancreatic cancer, renal cancer, small cell lung cancer, brain cancer, neural cancer, bone cancer, lymphoma, myeloma, gastrointestinal tract cancer, uterine cancer, breast cancer, leukemia, liver cancer, prostate cancer, skin cancer, and melanoma. In some embodiments, the cancer is soft tissue non-osteogenic sarcomas, chondrosarcoma, fibrosarcoma, or synovial sarcoma. In some embodiments, the cancer is specifically, a basal cell carcinoma, melanoma, thyroid adenocarcinomas, glial blastoma, pituitary tumors, oligodendrocytoma, bladder carcinoma, triple negative breast carcinoma, breast carcinoma, non-small cell lung carcinoma, small cell lung carcinoma, prostate carcinoma, neuroblastoma, or astrocytoma.

In some embodiments, the cancer is a sarcoma of bone, in the appendicular skeleton, the axial skeleton, and the skull, which includes non-specific bone sarcomas, osteosarcoma, osteogenic sarcomas, Ewing's sarcoma, or benign bone tumors.

In some embodiments, the controlled release formulation may be administered locally to a site of cancerous lesion (e.g., intratumorally, peritumorally or perilesionally), which may be, for example, a site of a metastatic cancer lesion.

Controlled Release Formulation

In some embodiments, the controlled release formulation may include at least 0.5-mM, or at least 1-mM, or at least 2-mM, or at least 3-mM, or at least 4-mM, or at least 5-mM, or at least 6-mM, or at least 7-mM, or at least 8-mM, or at least 9-mM, or at least 10-mM, or at least 11-mM, or at least 12-mM, or at least 13-mM, or at least 14-mM, or at least 15-mM, or at least 16-mM, or at least 17-mM, or at least 18-mM, or at least 19-mM, or at least 20-mM, or at least 21-mM, or at least 22-mM, or at least 23-mM of the OGFR antagonist. In some embodiments, when the OGFR antagonist is naloxone, naltrexone or their combination, a concentration of the OGFR antagonist in the formulation may be at least 0.2-mg/ml, or at least 0.4-mg/ml, or at least 0.8-mg/ml, or at least 1.2-mg/ml, or at least 1.6-mg/ml, or at least 2.0-mg/ml, or at least 2.4-mg/ml, or at least 2.8-mg/ml, or at least 3.2-mg/ml, or at least 3.6-mg/ml, or at least 4.0-mg/ml, or at least 4.4-mg/ml, or at least 4.8-mg/ml, or at least 5.2-mg/ml, or at least 5.6-mg/ml, or at least 6.0-mg/ml, or at least 6.4-mg/ml, or at least 6.8-mg/ml, or at least 7.2-mg/ml, or at least 7.6-mg/ml, or at least 8.0-mg/ml, or at least 8.4-mg/ml, or at least 8.8-mg/ml, or at least 9.2-mg/ml.

In some embodiments, the controlled release formulation may be a liquid formulation.

In some embodiments, the controlled release formulation may be a percutaneous formulation, i.e., a formulation for a percutaneous mode of administration.

In some embodiments, the controlled release formulation may be configured to release the OGFR antagonist, such as naloxone, naltrexone or their combination, over a period of 24-hours, 48-hours, 72-hours, 96-hours, 120-hours, 144-hours, or 168-hours.

In some embodiments, the controlled release formulation possesses a particular level of flowability. In some embodiments, the control release formulation can pass through a 27-G, 25-G, 23-G, 22-G, 21-G, or 18-G needle.

In some embodiments, the controlled release formulation may be such that it does not dissipate from the site of the local administering, which may be, for example, a site of a metastatic cancer lesion, while the OGFR antagonist, such as naloxone, naltrexone or their combination, is being released. Preferably, the controlled release formulation has a release rate of 0.075-mg/hr$^{1/2}$ to 0.3-mg/hr$^{1/2}$ and more preferably, a release rate of no more than 0.1788 mg/min.

In some embodiments, at least one pharmaceutically acceptable carrier in the formulation may be a salt of alginic acid (i.e., an alginate), which may optionally be included in an amount of 5% to 80% (w/w). The alginate may serve as a carrier and also a release rate controlling agent in the formulation.

In some embodiments, at least one pharmaceutically acceptable carrier in the formulation may include at least one natural gum. Non-limiting examples of natural gums include agar, alginic acid, sodium alginate, carrageenan, gum Arabic, gum ghatti, gum tragacanth, karaya gum, guar gum, locust bean gum, beta-glucan, dammar gum, glucomannan, psyllium seed husks, tara gum, gellan gum and xanthan gum.

In some embodiments, at least one pharmaceutically acceptable carrier in the formulation may include gum Arabic, which may optionally be included an amount of 6% to 60% (w/w) and which may serve as a carrier and also a release rate controlling agent in the formulation.

In some embodiments, the at least one pharmaceutically acceptable carrier in the formulation may include at least one inorganic lanthanum salt. In some embodiments, at least one pharmaceutically acceptable carrier in the formulation may include lanthanum carbonate, which may optionally be present in an amount of 5% to 65% (w/w) and which may serve as a carrier and also a release rate controlling agent in the formulation. In some embodiments, the at least one pharmaceutically acceptable carrier may include at least one iron salt. Suitable iron excipients are disclosed, for example, in U.S. Patent Application No. 2022-0016312, which is incorporated herein by reference in its entirety. In some embodiments, the at least one iron salt may include ferric sulfate, such as Fe(II) or Fe(III) sulfate, which may be present from 0% to 15% (w/w/) and provides stability to the carrier.

In some embodiments, the at least one pharmaceutically acceptable carrier may include at least one titanium salt. Suitable titanium salts are disclosed, for example, titanium oxide. In some embodiments, the at least one iron excipient may include ferric sulfate which may optionally be present from 0% to 15% (w/w) and which may provide color, stability and also contrast when imaging using CT.

In some embodiments, the at least one pharmaceutically acceptable carrier may include at least one sodium phosphate salt. Suitable sodium phosphate salts include sodium phosphate dibasic, sodium phosphate monobasic, and sodium phosphate dibasic dihydrate. In some embodiments, the at least one sodium phosphate salt may include sodium phosphate dibasic which may optionally be present from 0% to 10% (w/w) and which serves a release rate controlling agent.

In some embodiments, the at least one pharmaceutically acceptable carrier may include a sodium alginate, gum Arabic, lanthanum carbonate, sodium phosphate dibasic, ferric sulfate, and titanium oxide. Suitable carriers can be combined with the formulation in bead, microsphere or nanoparticle form, and can be made of natural and/or synthetic biocompatible polymers.

Examples of suitable biocompatible polymers include hyaluronic acid, collagen, tricalcium phosphate, chondroitin sulfate, polybutyrate, polylactide, polyglycolide, and lactide/glycolide copolymers, and mixtures or copolymers thereof. Suitable carriers also include on-polymer systems such as carboxylic acids, fatty acids, phospholipids, amino acids, lipids such as sterols, hydrogel release system; silastic system; peptide-based system; implants and the like.

In one embodiment, the carrier is a hygroscopic collagen-based carrier such as a collagen sponge, a collagen scaffold, a powdered collagen, or a collagen-based gelatin hydrogel.

In another embodiment, the carrier is a hydrophilic hydrogel-based carrier (e.g., poly lactic acid, poly glycolic acid), which allows an OGFR antagonist (e.g., naloxone or naltrexone or a functional derivative thereof) infused therein to be released over a period of time.

In another embodiment, the carrier is a carrier composed of a tri-block co-polymer comprising a central block of PLA (poly-(lactic acid) flanked by two blocks of PEG-(poly-(ethylene glycol).

In still another embodiment, the carrier is albumin, a derivative or fragment of albumin that maintains the naloxone/morphine binding site located at the interface between the IA and IIA domains, and/or maintains the naloxone binding site around tryptophan (Trp)-214, that binds an OGFR antagonist such as naloxone or naltrexone or a functional derivative thereof and allows for a slow release of the OGFR antagonist.

In still another embodiment, methyl cellulose, and an inert gel, for example, that binds an OGFR antagonist such as naloxone or naltrexone or a functional derivative thereof and allows for a slow release of the antagonist.

In another embodiment, the carrier is a carrier composed of PGA (poly-(glycolic acid)-PLGA (poly-(lactic glycolic acid)) spheres, which can encapsulate an OGFR antagonist to provide for immediate, delayed or sustained release.

Suitable carriers can be in bead, microsphere or nanoparticle form, and can be made of natural and/or synthetic biocompatible polymers. Examples of suitable biocompatible polymers include hyaluronic acid, collagen, tricalcium phosphate, chondroitin sulfate, polybutyrate, polylactide, polyglycolide, and lactide/glycolide copolymers, and mixtures or copolymers thereof. Suitable carriers also include on-polymer systems such as carboxylic acids, fatty acids, phospholipids, amino acids, lipids such as sterols, hydrogel release system; silastic system; peptide-based system; implants and the like.

In one embodiment, the carrier is a hygroscopic collagen-based carrier such as a collagen sponge, a collagen scaffold, a powdered collagen, or a collagen-based gelatin hydrogel.

In another embodiment, the carrier is a hydrophilic hydrogel-based carrier (e.g., poly lactic acid, poly glycolic acid), which allows an OGFR antagonist (e.g., naloxone or naltrexone or a functional derivative thereof) infused therein to be released over a period of time.

In another embodiment, the carrier is a carrier composed of a tri-block co-polymer comprising a central block of PLA (poly-(lactic acid) flanked by two blocks of PEG-(poly-(ethylene glycol).

In still another embodiment, the carrier is albumin, a derivative or fragment of albumin that maintains the naloxone/morphine binding site located at the interface between the IA and IIA domains, and/or maintains the naloxone binding site around tryptophan (Trp)-214, that binds an OGFR antagonist such as naloxone or naltrexone or a functional derivative thereof and allows for a slow release of the OGFR antagonist. In still another embodiment, methyl cellulose, and an inert gel, for example, that binds an OGFR antagonist such as naloxone or naltrexone or a functional derivative thereof and allows for a slow release of the antagonist.

In another embodiment, the carrier is a carrier composed of PGA (poly-(glycolic acid)-PLGA (poly-(lactic glycolic acid)) spheres, which can encapsulate an OGFR antagonist to provide for immediate, delayed or sustained release.

In some embodiments, a pharmaceutical composition disclosed herein comprises one or more "pharmaceutically acceptable carriers," such as an aqueous carrier, buffer, antioxidants, and/or diluents. In some embodiments, the pharmaceutical compositions comprise an OGFR antagonist in an ethanol (EtOH) based saline solution. In some embodiments, the pharmaceutical compositions comprise more than about 100 mM of the OGFR antagonist in the ethanol based saline solution. In some embodiments, the pharmaceutical compositions comprises about 10-mM to about 150-mM of the OGFR antagonist in the ethanol based saline solution. In some embodiments, the pharmaceutical compositions comprise about 20-mM to about 140-mM of the OGFR antagonist in the ethanol based saline solution. In some embodiments, the pharmaceutical compositions comprise about 30-mM to about 130-mM of the OGFR antagonist in the ethanol based saline solution. In some embodiments, the pharmaceutical compositions comprise about 40-mM to about 120-mM of the OGFR antagonist in the ethanol based saline solution. In some embodiments, the pharmaceutical compositions comprise about 50-mM to about 110-mM of the OGFR antagonist in the ethanol based saline solution. In some embodiments, the pharmaceutical compositions comprise about 10-mM to about 110-mM of the OGFR antagonist in the ethanol based saline solution. In some embodiments, the pharmaceutical compositions comprise more than 100-mM of the OGFR antagonist in the ethanol based saline solution. In some embodiments, the OGFR antagonist comprises about 100-mM naloxone, naltrexone, a functional derivative or analog thereof in the ethanol based saline solution.

In some embodiments, the acidified saline-based solution exhibits a pH from about 4.5 to about 7.4. In some embodiments, the acidified saline-based solution exhibits a pH from about 5.5 to about 7.4. In some embodiments, the acidified saline-based solution exhibits a pH from about 6.5 to about 7.4.

In some embodiments, the diluent is an ethanol based saline solution. In some embodiments, the ethanol based saline solution comprises from about 1% volume/volume (v/v) ethanol to about 80% v/v ethanol. In some embodiments, the ethanol based saline solution comprises from about 5% volume/volume (v/v) ethanol to about 80% v/v ethanol. In some embodiments, the ethanol based saline solution comprises from about 10% volume/volume (v/v) ethanol to about 80% v/v ethanol. In some embodiments, the ethanol based saline solution comprises from about 15% volume/volume (v/v) ethanol to about 80% v/v ethanol. In some embodiments, the ethanol based saline solution comprises from about 25% volume/volume (v/v) ethanol to about 80% v/v ethanol. In some embodiments, the ethanol based saline solution comprises from about 30% volume/volume (v/v) ethanol to about 80% v/v ethanol. In some embodiments, the ethanol based saline solution comprises from about 35% volume/volume (v/v) ethanol to about 80% v/v ethanol. In some embodiments, the ethanol based saline solution comprises from about 40% volume/volume (v/v) ethanol to about 80% v/v ethanol. In some embodiments, the ethanol based saline solution comprises from about 40% volume/volume (v/v) ethanol to about 70% v/v ethanol.

In some embodiments, the ethanol based saline solution comprises about 1% volume/volume (v/v) ethanol. In some embodiments, the ethanol based saline solution comprises about 2% volume/volume (v/v) ethanol. In some embodiments, the ethanol based saline solution comprises about 3% volume/volume (v/v) ethanol. In some embodiments, the ethanol based saline solution comprises about 4% volume/volume (v/v) ethanol. In some embodiments, the ethanol based saline solution comprises about 5% volume/volume (v/v) ethanol. In some embodiments, the ethanol based saline solution comprises about 6% volume/volume (v/v) ethanol. In some embodiments, the ethanol based saline solution comprises about 7% volume/volume (v/v) ethanol. In some embodiments, the ethanol based saline solution comprises about 8% volume/volume (v/v) ethanol. In some embodiments, the ethanol based saline solution comprises about 9% volume/volume (v/v) ethanol. In some embodiments, the ethanol based saline solution comprises about 10% volume/volume (v/v) ethanol. In some embodiments, the ethanol based saline solution comprises about 20% volume/volume (v/v) ethanol. In some embodiments, the ethanol based saline solution comprises about 30% volume/volume (v/v) ethanol. In some embodiments, the ethanol based saline solution comprises about 40% volume/volume (v/v) ethanol. In some embodiments, the ethanol based saline solution comprises about 50% volume/volume (v/v) ethanol. In some embodiments, the ethanol based saline solution comprises about 60% volume/volume (v/v) ethanol. In some embodiments, the ethanol based saline solution comprises about 70% volume/volume (v/v) ethanol. In some embodiments, the ethanol based saline solution comprises about 80% volume/volume (v/v) ethanol.

In some embodiments, the ethanol based saline solution comprises a phosphate buffered saline solution, a borate buffered saline solution, a Tris buffered saline solution, or a carbonate buffered saline solution.

In some embodiments, the saline solution comprises a salt and water. In some embodiments, the salt of the saline solution comprises sodium chloride or potassium chloride. In some embodiments, the saline solution comprises from about 0.7% w/w salt to about 1.5% w/w salt. In some embodiments, the saline solution comprises about 0.7% salt. In some embodiments, the saline solution comprises about 0.8% salt. In some embodiments, the saline solution comprises about 0.9% salt. In some embodiments, the saline solution comprises about 1.0% salt. In some embodiments, the saline solution comprises about 1.1% salt. In some embodiments, the saline solution comprises about 1.2% salt. In some embodiments, the saline solution comprises about 1.3% salt. In some embodiments, the saline solution comprises about 1.4% salt. In some embodiments, the saline solution comprises about 1.5% salt.

The OGFR antagonist may be combined or coordinately administered with a suitable carrier or vehicle depending on the route of administration. The term "pharmaceutically acceptable carrier" refers to a carrier that is conventionally used in the art to facilitate the storage, administration, and/or the healing effect of an active agent of a pharmaceutical composition.

A water-containing liquid carrier can comprise pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories can be found in the U.S. Pharmacopeia National Formulary, 1857-1859, and (1990). Some examples of the materials which can serve as pharmaceutically acceptable carriers are sugars, such as lactose, glucose and sucrose; cyclodextrins, including alpha-cyclodextrin, beta-cyclodextrin, and gamma-cyclodextrin; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer's solution, ethyl alcohol and phosphate buffer solutions, as well as other nontoxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents.

In some embodiments, the pharmaceutical composition comprises preservatives and antioxidants. Examples of pharmaceutically acceptable antioxidants include water soluble antioxidants such as ascorbic acid, cysteine hydrochloride, sodium bisulfite, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), sorbitol, tartaric acid, phosphoric acid and the like.

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art. Examples of filling agents include lactose monohydrate, lactose anhydrous, and various starches; examples of binding agents include various celluloses and cross-linked polyvinylpyrrolidone, microcrystalline cellulose such as Avicel™, PH101 microcrystalline cellulose and/or Avicel™, PH102 microcrystalline cellulose, and silicified microcrystalline cellulose such as ProSolv SMCC™. Suitable lubricants, including agents that act on the flow-ability of the powder to be compressed, may include colloidal silicon dioxide such as Aerosil® 200 (colloidal silicon dioxide), talc, stearic acid, magnesium stearate, calcium stearate, and silica gel. Examples of sweeteners may include any natural or artificial sweetener, such as sucrose, xylitol, sodium saccharin, cyclamate, aspartame, and acesulfame. Examples of flavoring agents are Monoammonium Glycyrrhizinate such as Magnasweet™ (a flavoring composition containing Monoammonium Glycyrrhizinate and trademark of MAFCO), bubble gum flavor, and fruit flavors, and the like. Examples of preservatives include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Any pharmaceutical formulation used for therapeutic administration can be sterile. Sterility is readily accomplished by for example filtration through sterile filtration membranes (e.g., 0.2 micron membranes). Any pharmaceutically acceptable sterility method can be used in the formulation.

The pharmaceutical composition comprising an OGFR antagonist derivatives or salts thereof will be formulated and dosed in a fashion consistent with good medical practice, taking into account the clinical condition of the individual patient, the method of administration, the scheduling of administration, and other factors known to those in the art.

A variety of administration routes are available. The pharmaceutical composition of the invention may be practiced using any mode of administration that is medically acceptable, meaning any mode that produces effective levels of the active ingredients without causing clinically unacceptable adverse effects. Accordingly, the pharmaceutical compositions can be administered to a subject parenterally, intraperitoneally, transdermally, intramuscularly, intratumorally, subcutaneously, intra-adiposally, intra-articularly, or intrathecally.

Modes of administration include topical, intradermal, or parenteral routes. The term "parenteral" includes subcutaneous, percutaneous, intravenous, intramuscular, or infusion.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's solution or fixed 25 oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In some embodiments, the controlled release formulation may be administered locally to a site (e.g., intratumorally, peritumorally, or perilesionally), such as a site of a metastatic cancer lesion, in a subject via percutaneous injection, any minimally invasive procedure, or via laparoscopy. The controlled release formulation may be such that it does not dissipate from the site of percutaneous injection. The act of local administering such as percutaneous injection to the site, such as the site of a metastatic cancer lesion, may be repeated for as long is tolerable to the patient and effective for reducing tumor, including but not limited to at least one additional time, or at least two time, or at least three times, or at least four times.

In some embodiments, the controlled release is administered locally at a local dosage of the OGFR antagonist, such as naloxone, naltrexone or their combination, of about 0.5-µM to about 20-mM. In some embodiments, the local dosage of about 1-mM to about 10-mM. In some embodiments, the local dosage may be 1-mM, 1.5-mM, 2.0-mM, 3.0-mM, 4.0-mM, 5.0-mM, 6.0-mM, 7.0-mM, 8.0-mM, 9.0-mM, 9.0-mM, 10.0-mM, 11.0-mM, 12.0-mM, 13.0-mM, 14.0-mM, 15.0-mM, 16.0-mM, 17.0-mM, 18.0-mM, 19.0-mM, 20.0-mM, 21.0-mM, 22.0-mM, and/or 23.0 mM.

In some embodiments, the OGFR antagonist is administered with a carrier, and the carrier volume may be from about 0.1-cubic centimeter (cc) to about 20-cc, from about 0.25-cc to about 15-cc, from about 0.5-cc to about 10-cc, from about 1-cc to about 10-cc, from about 2-cc to about 10-cc. The corresponding amount of the OGFR antagonist in the carrier may be from about 0.2 mg per cc, 0.5 mg per cc, 1.0 mg per cc, 2.0 mg per cc, 3.0 mg per cc, 4.0 mg per cc, 5.0 mg per cc, 6.0 mg per cc, 7.0 mg per cc, 8.0 mg per cc, 9.0 mg per cc, and/or 10.0 mg per cc.

The total amount of the OGFR antagonist naloxone hydrochloride in 0.5-cc of the carrier may be 0.1-mg for a 0.5-mM concentration, 0.2-mg for a 1-mM concentration, 0.4-mg for a 2-mM concentration, 0.8-mg for a 2.5-mM concentration, 0.6-mg for a 3-mM concentration, 0.8-mg for a 4-mM concentration, 1.0-mg for a 5-mM concentration, 1.2-mg for a 6-mM concentration, 1.4-mg for a 7-mM concentration, 1.6-mg for a 8-mM concentration, 1.8-mg for a 9-mM concentration, 2.0-mg for a 10-mM concentration, 2.2-mg for a 11-mM concentration, 2.4-g for a 12-mM concentration, 2.6-mg for a 13-mM concentration, 2.8-mg for a 14-mM concentration, 3.0-mg for a 15-mM concentration, 3.2-mg for a 16-mM concentration, 3.4-mg for a 17-mM concentration, 3.6-mg for a 18-mM concentration, 3.8-mg for a 19-mM concentration, 4.0-mg for a 20-mM concentration, 4.2-mg for a 21-mM concentration, 4.4-mg for a 22-mM concentration, 4.6-mg for a 23-mM concentration, 4.8-mg for a 24-mM concentration, 5.0-mg for a 25-mM concentration, 5.2-mg for a 26-mM concentration, 5.4-mg for a 27-mM concentration. The total amount of the OGFR antagonist naloxone hydrochloride in 1-cc of the carrier may be 0.2-mg for a 0.5-mM concentration, 0.4-mg for a 1-mM concentration, 0.8-mg for a 2-mM concentration, 1.0-mg for a 2.5-mM concentration, 1.2-mg for a 3-mM concentration, 1.6-mg for a 4-mM concentration, 2.0-mg for a 5-mM concentration, 2.4-mg for a 6-mM concentration, 2.8-mg for a 7-mM concentration, 3.2-mg for a 8-mM concentration, 3.6-mg for a 9-mM concentration, 4.0-mg for a 10-mM concentration, 4.4-mg for a 11-mM concentration, 4.8-g for a 12-mM concentration, 5.2-mg for a 13-mM concentration, 5.6-mg for a 14-mM concentration, 6.0-mg for a 15-mM concentration, 6.4-mg for a 16-mM concentration, 6.8-mg for a 17-mM concentration, 7.2-mg for a 18-mM concentration, 7.6-mg for a 19-mM concentration, 8.0-mg for a 20-mM concentration, 8.4-mg for a 21-mM concentration, 8.8-mg for a 22-mM concentration, 9.2-mg for a 23-mM concentration, 9.6-mg for a 24-mM concentration, 10.0-mg for a 25-mM concentration, 10.4-mg for a 26-mM concentration, 10.8-mg for a 27-mM concentration. The total amount of the OGFR antagonist naloxone hydrochloride in 3-cc of the carrier may be 0.6-mg for a 0.5-mM concentration, 1.2-mg for a 1-mM concentration, 2.4-mg for a 2-mM concentration, 3.0-mg for a 2.5-mM concentration, 3.6-mg for a 3-mM concentration, 4.8-mg for a 4-mM concentration, 6.0-mg for a 5-mM concentration, 7.2-mg for a 6-mM concentration, 8.4-mg for a 7-mM concentration, 9.6-mg for a 8-mM concentration, 10.8-mg for a 9-mM concentration, 12.0-mg for a 10-mM concentration, 13.2-mg for a 11-mM concentration, 14.4-g for a 12-mM concentration, 15.6-mg for a 13-mM concentration, 16.8-mg for a 14-mM concentration, 18.0-mg for a 15-mM concentration, 19.2-mg for a 16-mM concentration, 20.4-mg for a 17-mM concentration, 21.6-mg for a 18-mM concentration, 22.8-mg for a 19-mM concentration, 24.0-mg for a 20-mM concentration, 25.2-mg for a 21-mM concentration, 26.4-mg for a 22-mM concentration, 27.6-mg for a 23-mM concentration, 28.8-mg for a 24-mM concentration, 30.0-mg for a 25-mM concentration, 31.6-mg for a 26-mM concentration, 32.8-mg for a 27-mM concentration.

The total amount of the controlled release formulation administered can be achieved by adding any of the concentrations together, such that to achieve 4.5-cc of a 10-mM concentration for the controlled release formulation one could add the following using the concentrations listed above by way of example: 1) 0.5-cc of the controlled release formulation containing 2-mg of naloxone hydrochloride for a 10-mM concentration, 2) 1-cc of the controlled release formulation containing 4-mg of naloxone hydrochloride for a 10-mM concentration, 3) 3-cc of the controlled release formulation containing 12.0-mg of naloxone hydrochloride for a concentration of 10-mM. When added together, the final volume would be 4.5-cc and contain 18-mg of naloxone hydrochloride for a 10-mM concentration.

Likewise, different concentrations can be added together to achieve additional useful working volumes and concentrations, such that to achieve 1.5-cc of a 17.5-mM concentration for the controlled release formulation one could add the following using the concentrations listed above: 1) 0.5-cc of the controlled release formulation containing 0.2-mg of naloxone hydrochloride for a 1-mM concentration and 2) 1-cc of the controlled release formulation containing 6.8-mg of naloxone hydrochloride for a 17-mM concentration. When added together, the final volume would be 1.5-cc and contain 7-mg of naloxone hydrochloride for a 17.5-mM concentration. This process can be repeated to achieve any concentration for a useful volume of the controlled release formulation. Further, as is consistent in common medical practice, the volumes of material can be adjusted to achieve the desired concentration to volume ratio for the controlled release formulation, such that a 0.75-cc fraction of the 3-cc of the controlled release formulation with a concentration of 9-mM would yield a useful formulation with a 2.25-mM concentration containing 2.7-mg of naloxone hydrochloride (e.g., a 0.75-cc volume at a concentration of 2.25-mM that contains 2.7-mg of naloxone hydrochloride). Thus, using the additive method and the fractional method shown above, any concentration of the controlled release formulation can be achieved for any useful volume to be administered.

The methods and compositions herein may be provided in the form of a kit. A "kit" is herein defined as a package and containing several individual parts that show a complementary effect when applied together. In this aspect, the effect achieved by a kit and the pharmaceutical composition are similar. The kit may optionally include instructions for using the pharmaceutical compositions.

The present invention is further illustrated by, though in no way limited to, the following examples.

The following design parameters were used to determine a design space in which the elution/release rate was minimized (≥0.075 and ≤0.3-mg/hr$^{1/2}$), ≤100% of the drug release occurred over 24-hours, the material was hemostatic, the material could be injected using a syringe, and could be viewed using ultrasound and computed tomography (CT). A summary of the compositions that met these design criteria are listed below in Table I.

TABLE I

| Combinations of Components for the Preferred Formulation (ZM001) | | | | | | | | | | |
|---|---|---|---|---|---|---|---|---|---|---|
| Component | | | | | | | | | | |
| | Percentage of Component (w/w) | | | | | | | | | |
| Sodium alginate | 50.0% | 50.1% | 50.2% | 50.3% | 50.4% | 50.5% | 50.6% | 50.7% | 50.8% | 50.9% |
| | 51.0% | 51.1% | 51.2% | 51.3% | 51.4% | 51.5% | 51.6% | 51.7% | 51.8% | 51.9% |
| | 52.0% | 52.1% | 52.2% | 52.3% | 52.4% | 52.5% | 52.6% | 52.7% | 52.8% | 52.9% |
| | 53.0% | 53.1% | 53.2% | 53.3% | 53.4% | 53.5% | 53.6% | 53.7% | 53.8% | 53.9% |
| | 54.0% | 54.1% | 54.2% | 54.3% | 54.4% | 54.5% | 54.6% | 54.7% | 54.8% | 54.9% |
| | 55.0% | 55.1% | 55.2% | 55.3% | 55.4% | 55.5% | 55.6% | 55.7% | 55.8% | 55.9% |
| gum Arabic | 10.0% | 10.1% | 10.2% | 10.3% | 10.4% | 10.5% | 10.6% | 10.7% | 10.8% | 10.9% |
| | 11.0% | 11.1% | 11.2% | 11.3% | 11.4% | 11.5% | 11.6% | 11.7% | 11.8% | 11.9% |
| | 12.0% | 12.1% | 12.2% | 12.3% | 12.4% | 12.5% | 12.6% | 12.7% | 12.8% | 12.9% |
| | 13.0% | 13.1% | 13.2% | 13.3% | 13.4% | 13.5% | 13.6% | 13.7% | 13.8% | 13.9% |
| | 14.0% | 14.1% | 14.2% | 14.3% | 14.4% | 14.5% | 14.6% | 14.7% | 14.8% | 14.9% |
| | 15.0% | 15.1% | 15.2% | 15.3% | 15.4% | 15.5% | 15.6% | 15.7% | 15.8% | 15.9% |
| lanthanum | 23.0% | 23.1% | 23.2% | 23.3% | 23.4% | 23.5% | 23.6% | 23.7% | 23.8% | 23.9% |
| carbonate | 24.0% | 24.1% | 24.2% | 24.3% | 24.4% | 24.5% | 24.6% | 24.7% | 24.8% | 24.9% |
| | 25.0% | 25.1% | 25.2% | 25.3% | 25.4% | 25.5% | 25.6% | 25.7% | 25.8% | 25.9% |
| | 26.0% | 26.1% | 26.2% | 26.3% | 26.4% | 26.5% | 26.6% | 26.7% | 26.8% | 26.9% |
| | 27.0% | 27.1% | 27.2% | 27.3% | 27.4% | 27.5% | 27.6% | 27.7% | 27.8% | 27.9% |
| | 28.0% | 28.1% | 28.2% | 28.3% | 28.4% | 28.5% | 28.6% | 28.7% | 28.8% | 28.9% |
| sodium | 0.0% | 0.1% | 0.2% | 0.3% | 0.4% | 0.5% | 0.6% | 0.7% | 0.8% | 0.9% |
| phosphate | 1.0% | 1.1% | 1.2% | 1.3% | 1.4% | 1.5% | 1.6% | 1.7% | 1.8% | 1.9% |
| dibasic | 2.0% | 2.1% | 2.2% | 2.3% | 2.4% | 2.5% | 2.6% | 2.7% | 2.8% | 2.9% |
| | 3.0% | 3.1% | 3.2% | 3.3% | 3.4% | 3.5% | 3.6% | 3.7% | 3.8% | 3.9% |
| | 4.0% | 4.1% | 4.2% | 4.3% | 4.4% | 4.5% | 4.6% | 4.7% | 4.8% | 4.9% |
| | 5.0% | 5.1% | 5.2% | 5.3% | 5.4% | 5.5% | 5.6% | 5.7% | 5.8% | 5.9% |

TABLE I-continued

Combinations of Components for the Preferred Formulation (ZM001)

| Component | | | | | | | | | | |
|---|---|---|---|---|---|---|---|---|---|---|
| titanium oxide | 1.0% | 1.1% | 1.2% | 1.3% | 1.4% | 1.5% | 1.6% | 1.7% | 1.8% | 1.9% |
| | 2.0% | 2.1% | 2.2% | 2.3% | 2.4% | 2.5% | 2.6% | 2.7% | 2.8% | 2.9% |
| | 3.0% | 3.1% | 3.2% | 3.3% | 3.4% | 3.5% | 3.6% | 3.7% | 3.8% | 3.9% |
| | 4.0% | 4.1% | 4.2% | 4.3% | 4.4% | 4.5% | 4.6% | 4.7% | 4.8% | 4.9% |
| | 5.0% | 5.1% | 5.2% | 5.3% | 5.4% | 5.5% | 5.6% | 5.7% | 5.8% | 5.9% |
| | 6.0% | 6.1% | 6.2% | 6.3% | 6.4% | 6.5% | 6.6% | 6.7% | 6.8% | 6.9% |
| ferric (III) sulfate | 1.0% | 1.1% | 1.2% | 1.3% | 1.4% | 1.5% | 1.6% | 1.7% | 1.8% | 1.9% |
| | 2.0% | 2.1% | 2.2% | 2.3% | 2.4% | 2.5% | 2.6% | 2.7% | 2.8% | 2.9% |
| | 3.0% | 3.1% | 3.2% | 3.3% | 3.4% | 3.5% | 3.6% | 3.7% | 3.8% | 3.9% |
| | 4.0% | 4.1% | 4.2% | 4.3% | 4.4% | 4.5% | 4.6% | 4.7% | 4.8% | 4.9% |
| | 5.0% | 5.1% | 5.2% | 5.3% | 5.4% | 5.5% | 5.6% | 5.7% | 5.8% | 5.9% |
| | 6.0% | 6.1% | 6.2% | 6.3% | 6.4% | 6.5% | 6.6% | 6.7% | 6.8% | 6.9% |
| Component (mg/mL) | | | | | | | | | | |
| naloxone hydrochloride | 1.00 | 1.10 | 1.20 | 1.30 | 1.40 | 1.50 | 1.60 | 1.70 | 1.80 | 1.90 |
| | 2.00 | 2.10 | 2.20 | 2.30 | 2.40 | 2.50 | 2.60 | 2.70 | 2.80 | 2.90 |
| | 3.00 | 3.10 | 3.20 | 3.30 | 3.40 | 3.50 | 3.60 | 3.70 | 3.80 | 3.90 |
| | 4.00 | 4.10 | 4.20 | 4.30 | 4.40 | 4.50 | 4.60 | 4.70 | 4.80 | 4.90 |
| | 5.00 | 5.10 | 5.20 | 5.30 | 5.40 | 5.50 | 5.60 | 5.70 | 5.80 | 5.90 |
| | 6.00 | 6.10 | 6.20 | 6.30 | 6.40 | 6.50 | 6.60 | 6.70 | 6.80 | 6.90 |
| | 7.00 | 7.10 | 7.20 | 7.30 | 7.40 | 7.50 | 7.60 | 7.70 | 7.80 | 7.90 |
| | 8.00 | 8.10 | 8.20 | 8.30 | 8.40 | 8.50 | 8.60 | 8.70 | 8.80 | 8.90 |
| | 9.00 | 9.10 | 9.20 | 9.30 | 9.40 | 9.50 | 9.60 | 9.70 | 9.80 | 9.90 |
| | 10.00 | 10.10 | 10.20 | 10.30 | 10.40 | 10.50 | 10.60 | 10.70 | 10.80 | 10.90 |

Example 1

In a preferred example, named ZM001, the controlled release formulation comprises a powder component and a diluent which are combined by mixing shortly before use. The powder component in the preferred example ZM001 of the controlled release formulation contains the following components, based on the needs of the tissue into which the controlled release formulation is injected: 1) 53.06% (w/w) sodium alginate, 2) 11.87% (w/w) gum Arabic, 3) 26.53% (w/w) lanthanum carbonate, 4) 2.97% (w/w) sodium phosphate dibasic, 5) 3.71% (w/w) titanium oxide, and 6) 1.86% (w/w) ferric (III) sulfate. The diluent component in the preferred example ZM001 of the controlled release formulation contains 5% (v/v) glacial acetic acid, 5% (v/v) 100% ethanol, 95% (v/v) saline, and 4-mg/mL of naloxone hydrochloride. These combinations are summarized in Table I. Before use, the diluent is added to the powder component in a ratio of 7.8:1. The controlled release formulation should be mixed until gelling occurs, which takes approximately 30-seconds, and then allowed to rest for about 2-minutes to achieve full hydration.

The release rate (mg/hr$^{1/2}$) and the percentage of the small molecule released were assessed using ultra precision liquid chromatography (UPLC). Table 2 shows the parameters used for the UPLC and FIG. 1 shows the results of UPLC for Example 1.

TABLE II

| | |
|---|---|
| Vessel size | 200-mL |
| Stirring rate | 50-rpm with micro paddle |
| Media | Water, degassed |
| Media volume | 80-mL |
| Sampling | canular |
| Sample volume | 1-mL, replaced with 1-mL of media |
| Analysis | UPLC |

The preferred embodiment ZM001 met the stated design criteria and was found to have the following properties: 1) a release rate of 0.1788-mg/hr$^{1/2}$ (FIG. 1) measured using UPLC, 2) 88.8% of the small molecule naloxone hydrochloride was released during a 24-hour period (FIG. 1) measured using UPLC, 3) the ZM001 formulation, via empirical evaluation, passed through 27-G, 25-G, 23-G, 22-G, 21-G, and 18-G needles using a 1-cc, 5-cc, or 10-cc syringe, 4) the ZM001 formulation could be visualized under ultrasound imaging (FIG. 2) and computed tomographic imaging (FIG. 3), and 5) finally, the hemostatic properties were assessed using the Clotting Time Assay, and it was found that the ZM001 formulation decreased clotting time by 54%.

The release rate was empirically modeled from data derived from using ultra performance liquid chromatography (UPLC). The data were fit using the Hixson-Crowell cube-root law for diffusion from a hydrogel, using the following equation (1):

$$\sqrt[3]{Q0} - \sqrt[3]{Qt} = K \times t \qquad (1)$$

In this equation, Q0 is the starting amount of naloxone, Qt is the amount of naloxone at some time (t), K is the rate constant, and t is time. K is a dimensionless constate derived empirically from the material properties of the controlled release carrier material. As such, K is an intrinsic property of a material, and the concentrations of the components listed in Table I, will produce a release rate between 0.075-mg/hr$^{1/2}$ to 0.3-mg/hr$^{1/2}$. Using linear regression, a best-fit line modeled on the Hixson-Crowell equation was found to be y=0.1603x+0.4066 and had an $R^2$=0.9332. This equation was used to determine the release rate of the naloxone as well as how much naloxone eluted out of the ZM001 material over 24-hours (FIG. 1)

The material properties of the ZM001 formulation were also assessed. Syneresis is the loss of fluid in a hydrogel material, which relates to the release rate and was found to be 1.3%. Viscosity and temperature were also assessed and were found to be non-linear (FIGS. 4 and 5). The maximum viscosity is equivalent to the gelling time, which was found to be 1000-sec (e.g., ~16.5 minutes). Formulation ZM001 is endothermic, which means the temperature decreased with respect to time, with a ~0.5° C. decrease in temperature occurring through 1000-sec (~16.5 min).

Example 2

In a preferred example, named ZM002, the controlled release formulation comprises a powder component and a diluent which are combined by mixing shortly before use. The powder component in the preferred example ZM002 of the controlled release formulation contains the following components, based on the needs of the tissue into which the controlled release formulation is injected: 1) 53.62% (w/w) sodium alginate, 2) 14.84% (w/w) gum Arabic, 3) 23.54% (w/w) lanthanum carbonate, 4) 2.5% (w/w) sodium phosphate dibasic, 5) 3.0% (w/w) titanium oxide, and 6) 2.0% (w/w) ferric (III) sulfate. The diluent component in the preferred example ZM001 of the controlled release formulation contains 5% (v/v) glacial acetic acid, 5% (v/v) 100% ethanol, 95% (v/v) saline, and 4-mg/mL of naloxone hydrochloride. These combinations are summarized in Table I. Before use, the diluent is added to the powder component in a ratio of 7.8:1. The controlled release formulation should be mixed until gelling occurs, which takes approximately 30-seconds, and then allowed to rest for about 2-minutes to achieve full hydration.

The preferred embodiment ZM002 meets the stated design criteria and is predicted to have the following properties: 1) a release rate of $0.1682\text{-mg/hr}^{1/2}$, 2) 83.0% of the small molecule naloxone hydrochloride is released during a 24-hour period.

Example 3

In a preferred example, named ZM003, the controlled release formulation comprises a powder component and a diluent which are combined by mixing shortly before use. The powder component in the preferred example ZM003 of the controlled release formulation contains the following components, based on the needs of the tissue into which the controlled release formulation is injected: 1) 45.38% (w/w) sodium alginate, 2) 10.44% (w/w) gum Arabic, 3) 36.19% (w/w) lanthanum carbonate, 4) 2.5% (w/w) sodium phosphate dibasic, 5) 3.0% (w/w) titanium oxide, and 6) 2.0% (w/w) ferric (III) sulfate. The diluent component in the preferred example ZM001 of the controlled release formulation contains 5% (v/v) glacial acetic acid, 5% (v/v) 100% ethanol, 95% (v/v) saline, and 4-mg/mL of naloxone hydrochloride. These combinations are summarized in Table I. Before use, the diluent is added to the powder component in a ratio of 7.8:1. The controlled release formulation should be mixed until gelling occurs, which takes approximately 30-seconds, and then allowed to rest for about 2-minutes to achieve full hydration.

The preferred embodiment ZM003 meets the stated design criteria and is predicted to have the following properties: 1) a release rate of $0.1992\text{-mg/hr}^{1/2}$, 2) 88.59% of the small molecule naloxone hydrochloride is released during a 24-hour period.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

---

What is claimed is:

1. A method of treating a cancer comprising locally administering at a site of a subject in need thereof an effective amount of a controlled release formulation comprising naloxone and at least one pharmaceutically acceptable carrier comprising sodium alginate, gum Arabic, and lanthanum carbonate, wherein said controlled release formulation comprises naloxone in an amount of at least 11 mM and said controlled release formulation provides a release rate of naloxone of $0.075\text{-mg/hr}^{1/2}$ to $0.3\text{-mg/hr}^{1/2}$.

2. The method of claim 1, wherein the cancer comprises at least one metastatic cancer lesion and said administering is performed locally at a site of the at least one metastatic cancer lesion of the subject.

3. The method of claim 1, wherein said administering is performed percutaneously.

4. The method of claim 1, wherein the formulation does not dissipate from the site of the administering after the administering is performed.

5. The method of claim 1, further comprising repeating said administering at the site.

6. The method of claim 1, wherein the cancer is selected from the group consisting of breast cancer, lung cancer, prostate cancer, and glioblastoma.

7. The method of claim 1, wherein the controlled release formulation comprises at least 12 mM of naloxone.

8. The method of claim 1, wherein the at least one pharmaceutically acceptable carrier further comprises at least one iron excipient.

9. The method of claim 8, wherein the at least one iron excipient further comprises ferric sulfate.

10. The method of claim 1, wherein the at least one pharmaceutically acceptable carrier further comprises ferric sulfate.

11. The method of claim 1, wherein the formulation is a liquid formulation.

12. The method of claim 1, wherein the at least one pharmaceutically acceptable carrier further comprises sodium phosphate.

13. The method of claim 12, wherein the sodium phosphate is sodium phosphate dibasic.

14. The method of claim 1, wherein the controlled release formulation comprises at least 12 mM naloxone.

15. The method of claim 1, wherein the controlled release formulation comprises at least 14 mM naloxone.

16. The method of claim 1, wherein an amount of lanthanum carbonate in the formulation is from 5% to 65% (w/w).

\* \* \* \* \*